(12) United States Patent
Kazerooni et al.

(10) Patent No.: US 7,883,546 B2
(45) Date of Patent: Feb. 8, 2011

(54) POWER GENERATING LEG

(75) Inventors: Homayoon Kazerooni, Berkeley, CA (US); Adam Zoss, Berkeley, CA (US); Nathan H. Harding, Oakland, CA (US); Russdon Angold, American Canyon, CA (US)

(73) Assignee: The Regents of the University of California, Oakland, CA (US)

( * ) Notice: Subject to any disclaimer, the term of this patent is extended or adjusted under 35 U.S.C. 154(b) by 579 days.

(21) Appl. No.: 11/716,135

(22) Filed: Mar. 9, 2007

(65) Prior Publication Data
US 2007/0233279 A1    Oct. 4, 2007

Related U.S. Application Data

(60) Provisional application No. 60/781,569, filed on Mar. 9, 2006.

(51) Int. Cl.
*A61F 2/74* (2006.01)
(52) U.S. Cl. .......................................... 623/27; 623/32
(58) Field of Classification Search ................... 623/32, 623/27
See application file for complete search history.

(56) References Cited

U.S. PATENT DOCUMENTS

| 406,328 | A | 7/1889 | Yagn |
|---|---|---|---|
| 420,178 | A | 1/1890 | Yagn |
| 420,179 | A | 1/1890 | Yang |
| 440,684 | A | 11/1890 | Yagn |
| 539,872 | A | 5/1895 | Kheiralla |
| 807,908 | A | 12/1905 | Bradstreet |

(Continued)

FOREIGN PATENT DOCUMENTS

CN    1586434 A    3/2005

(Continued)

OTHER PUBLICATIONS

International Search Report and Written Opinion mailed Jan. 28, 2008, for PCT Application No. PCT/US07/06122 filed Mar. 9, 2007, 12 pages.

(Continued)

*Primary Examiner*—Bruce E Snow
*Assistant Examiner*—Melissa Hoban
(74) *Attorney, Agent, or Firm*—Diederiks & Whitelaw, PLC

(57) ABSTRACT

A power generating leg, configurable to be coupled to a person's lower limb, comprising a thigh link, a shank link, a knee mechanism, a torque generator, and a power unit. The knee mechanism is connected to said thigh link and said shank link, and configured to allow flexion and extension movements of said thigh link and said shank link relative to each other. The torque generator is configured to generate torque between said shank link and said thigh link. The power unit is coupled to said torque generator, and configured to cause said torque generator to generate torque. When said power unit is in a power regeneration mode, said power unit causes said torque generator to generate a torque that opposes the angular velocity of said thigh link and said shank link relative to each other and said power unit converts a portion of the power associated with the product of said torque and said angular velocity of said shank link and thigh link relative to each other into electrical power to be stored in a storage device.

60 Claims, 16 Drawing Sheets

U.S. PATENT DOCUMENTS

| | | | |
|---|---|---|---|
| 979,243 | A | 12/1910 | Anderson |
| 1,308,675 | A | 7/1919 | Kelley |
| 4,647,004 | A | 3/1987 | Bihlmaier |
| 5,020,790 | A | 6/1991 | Beard et al. |
| 5,282,460 | A | 2/1994 | Boldt |
| 5,476,441 | A | 12/1995 | Durfee et al. |
| 5,658,242 | A | 8/1997 | McKay et al. |
| 5,662,693 | A | 9/1997 | Johnson et al. |
| 5,961,476 | A | 10/1999 | Betto et al. |
| 6,422,329 | B1 | 7/2002 | Kazerooni et al. |
| 6,500,210 | B1 | 12/2002 | Sabolich et al. |
| 6,676,707 | B2 | 1/2004 | Yih et al. |
| 6,807,869 | B2 | 10/2004 | Farringdon et al. |
| 6,821,233 | B1 | 11/2004 | Colombo et al. |
| 6,966,882 | B2 | 11/2005 | Horst |
| 7,048,707 | B2 | 5/2006 | Schwenn et al. |
| 7,111,704 | B2 | 9/2006 | Johnson |
| 7,153,242 | B2 | 12/2006 | Goffer |
| 7,313,463 | B2 | 12/2007 | Herr et al. |
| 2004/0102723 | A1* | 5/2004 | Horst ............................ 601/5 |
| 2004/0116839 | A1 | 6/2004 | Sarkodie-Gyan |
| 2005/0167178 | A1 | 8/2005 | Johnson |
| 2006/0046907 | A1 | 3/2006 | Rastegar et al. |
| 2006/0249315 | A1 | 11/2006 | Herr et al. |
| 2006/0260620 | A1 | 11/2006 | Kazerooni et al. |
| 2007/0043449 | A1 | 2/2007 | Herr et al. |
| 2007/0123997 | A1 | 5/2007 | Herr et al. |
| 2007/0162152 | A1 | 7/2007 | Herr et al. |
| 2008/0154165 | A1 | 6/2008 | Ashihara et al. |

FOREIGN PATENT DOCUMENTS

| | | |
|---|---|---|
| CN | 101094640 A | 12/2007 |
| WO | WO-2007/016781 A1 | 2/2007 |
| WO | WO 2007/025116 | 3/2007 |

OTHER PUBLICATIONS

International Search Report and Written Opinion mailed Aug. 15, 2007, for PCT Application No. PCT/US06/14227 filed Apr. 13, 2006, 13 pages.

International Search Report and Written Opinion mailed Aug. 7, 2007, for PCT Application No. PCT/US06/01981 filed Jan. 18, 2006, 11 pages.

First Chinese Office Action dated Apr. 27, 2009, for CN Application No. 200680006514.1, filed Jan. 18, 2006. 8 pages. (English translation, 8 pages).

U.S. Appl. No. 12/552,021, filed Sep. 1, 2009 for Herr et al.

U.S. Appl. No. 60/666,876, filed Mar. 1, 2005 for Herr et al.

U.S. Appl. No. 60/707,232, filed Aug. 10, 2005 for Donelan et al.

"Exoskeleton Prototype Project: Final Report on Phase I," (Oct. 1966). Contract No. N00014-66-C0051, Mechanical Equipment Branch, Mechanical Technology Laboratory, Research and Development Center, General Electric Company: Schenectady, New York, pp. 1-72.

"Machine Augmentation of Human Strength and Endurance: Hardiman I Prototype Project," (Jul. 1969). ONR Contract No. N00014-66-C0051, Specialty Materials Handling Products Operation, General Electric Company: Schenectady, New York, 60 pages.

"Research and Development Prototype for Machine Augmentation of Human Strength and Endurance: Hardiman I Project," (May 1971). ONR Contract No. N00014-66-C0051, Specialty Materials Handling Products Operation, General Electric Company, Schenectady, New York, pp. 1-25.

Arroyo, P. (Dec. 1998). "Design of a Minimally Actuated Assistive Walking Device," Masters of Science Thesis submitted to the Graduate School at the University of California, Berkeley, 25 pages.

Belforte, G. et al. "Pneumatic Active Gait Orthosis," *Mechatronics* 11:301-323.

Chu, A. (Apr. 2003). "Design Overview of 1st Generation Exoskeleton," Master of Science Thesis submitted to the Mechanical Engineering Department at the University of California, Berkeley, pp. 1-62.

Clark, D. C. et al. (Aug. 1962). "Exploratory Investigation of the Man Amplifier Concept," Technical Documentary Report No. AMRL-TDR-62-89, Behavioral Science Laboratory, Aerospace Medical Division, Air Force Systems Command, Wright-Patterson Air Force Base: Ohio, 81 pages.

Ferris, D. et al. (Aug. 2001) "An Ankle-foot Orthosis Powered by Artificial Muscles," *Proceedings of the 25th Annual Meeting of the American Society of Biomechanics*, 2 pages.

Harley, J. A. (Aug. 1995). "Design and Construction of an Underactuated Assistive Walking Device," Master of Science Thesis submitted to the Graduate School at the University of California, Berkeley, pp. 1-31.

Irby, S. et al. (Jun. 1999)."Automatic Control Design for a Dynamic Knee-Brace System," *IEEE Transactions on Rehabilitation Engineering* 7(2):135-139.

Johnson, D. et al. (1996). "Development of a Mobility Assist for the Paralyzed, Amputee, and Spastic Patient," *IEEE Proceedings of the 15th Southern Biomedical Engineering Conference*, pp. 67-70.

Kasaoka, K. et al. (2001). "Predictive Control Estimating Operator's Intention for Stepping-up Motion by Exoskeleton Type Power Assist System HAL." *Proceedings of the 2001 IEEE/RJS: International Conference on Intelligent Robots and Systems*, Maui, Hawaii, pp. 1578-1583.

Kawamoto, H. et al. (2002) "Power Assist System HAL-3 for Gait Disorder Person." Lecture Notes in Computer Science (LNCS), *Proceedings of the Eighth International conference on Computers Helping People with Special Needs (ICCHP)* 2398:196-203.

Kawamoto, H. et al. (2002). "Comfortable Power Assist Control Method for Walking Aid by HAL-3," *IEEE Proceedings of the International Conference on Systems, Man, and Cybernetics (SMC)*, 6 pages.

Lee, S. et al. (Oct. 2002). "Power Assist Control for Walking Aid with HAL-3 Based on EMG and Impedance Adjustment Around Knee Joint," *Proceedings of the IEEE/RJS International Conference on Intelligent Robots and Systems (IROS)*, Lausanne, Switzerland, pp. 1499-1504.

Lim, M. Z. M. (Dec. 2000). "An Analysis on the Performance of an Underactuated Lower Extremity Enhancer," Master of Science Thesis submitted to the Mechanical Engineering Department at the University of California, Berkeley, pp. 1-33.

Misuraca, J. et al. (Nov. 2001). "Lower Limb Human Muscle Enhancer," Proceedings of IMECE01: International Mechanical Engineering Conference and Exposition, New York, New York, pp. 1-7.

Mori, Y. (Apr. 2004). "Development of Straight Style Transfer Equipment for Lower Limbs Disabled," *Proceedings of the 2004 IEEE International Conference on Robotics and Automation*, New Orleans, Louisiana, pp. 2486-2491.

Morris, S. et al. (Oct. 2002). "Shoe-Integrated Sensor System for Wireless Gait Analysis and Real-Time Feedback," *Proceedings of the Second Joint EMBS/BMES Conference*, Houston, Texas, pp. 2468-2469.

Mosher, R. S. (Jan. 1967). "Handyman to Hardiman," Automotive Engineering Congress, Society of Automotive Engineers, Detroit, Michigan, pp. 1-12.

Naruse, K. et al. (Nov. 2003). "Design of Compact and Lightweight Wearable Power Assist Device," *Proceedings of IMECE '03, 2003 ASME International Mechanical Engineering Congress and Exposition*, Washington D.C., pp. 1-8.

Pratt, J. E. et al. (Apr. 2004). "The RoboKnee: An Exoskeleton for Enhancing Strength and Endurance During Walking," *Proceedings of the IEEE International Conference on robotics and Automation*, New Orleans, Louisiana, pp. 2430-2435.

Racine, J.-L. C. (2003). "Control of a Lower Exoskeleton for Human Performance Amplification," PhD Thesis submitted to the University of California, Berkeley, pp. 1-832.

Rehnmark, F. L. (May 1997). "Dynamic Simulation and Design of a Powered Underactuated Assistive Walking Device," Master of Science Thesis submitted to the Graduate School at the University of California, Berkeley, pp. 1-35.

Van Den Bogert, A. J. (Oct. 2003). "Exotendons for Assistance of Human Locomotion," *Biomedical Engineering Online* 2(17):1-8.

Vukobratovic, M. et al. (Jan. 1974). "Development of Active Anthropomorphic Exoskeletons," *Medical and Biological Engineering*, pp. 66-80.

Yamamoto, K. et al. (2002). "Development of Power Assisting Suit for Assisting Nurse Labor," *JSME International Journal*, Series C, 45(3):703-711.

Yamamoto, K. et al. (2003). "Development of Power Assisting Suit (Miniaturization of Supply System to Realize Wearable Suit)," *JSME International Journal*, Series C, 46(3):923-930.

Zoss, A. (2003). "Mechanical Design Implementation of an Exoskeleton," Master of Science Thesis submitted to the University of California, Berkeley, pp. 1-140.

U.S. Appl. No. 10/976,652, filed Oct. 29, 2004 for Kazerooni et al.

U.S. Appl. No. 11/404,719, filed Apr. 13, 2006 for Kazerooni et al.

\* cited by examiner

POWER GENERATING LEG

CROSS-REFERENCE TO RELATED APPLICATION

The present application claims priority to U.S. Provisional Application Ser. No. 60/781,569, titled POWER GENERATING LEGS, filed on Mar. 9, 2006, which is incorporated herein by reference in its entirety for all purposes.

This invention was made with Government support under Grant Contract No. DAAD19-01-0509 awarded by DARPA. The Government has certain rights to this invention.

BACKGROUND

1. Field

The present application relates generally to the field of power generating legs.

2. Related Art

A human walks in a cyclic motion. Opportunities exist, therefore, to provide a device that converts walking mechanical power into electrical power. In particular this application describes a power generating leg that is configured to be coupled to a person's lower limb and generate power as the person walks. The power generating leg described here can be an orthotic leg or a prosthetic leg. In some embodiments, the power generating leg is a leg of a robotic exoskeleton.

SUMMARY

In one exemplary embodiment, a power generating leg, configured to be coupled to a person's lower limb, comprising a thigh link, a shank link, a knee mechanism, a torque generator, and a power unit. The knee mechanism is connected to said thigh link and said shank link, and configured to allow flexion and extension movements of said thigh link and said shank link relative to each other. The torque generator is configured to generate torque between said shank link and said thigh link. The power unit is coupled to said torque generator, and configured to cause said torque generator to generate torque. When said power unit is in a power regeneration mode, said power unit causes said torque generator to generate a torque that opposes the angular velocity of said thigh link and said shank link relative to each other, and said power unit converts a portion of the power associated with the product of said torque and said angular velocity of said shank link and thigh link relative to each other into electrical power to be stored in a storage device.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
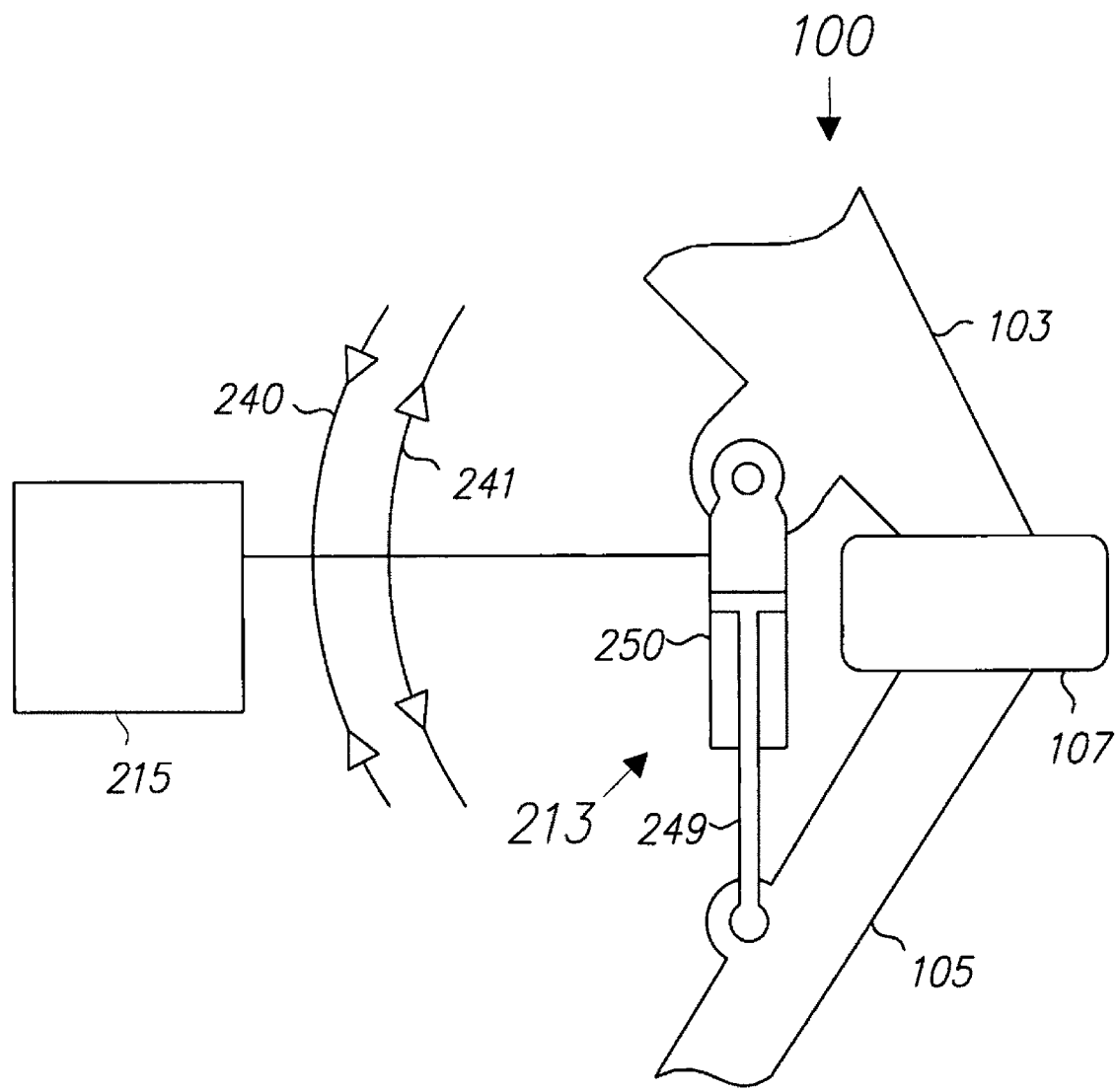
FIG. 1 is a side view of an exemplary embodiment of a power generating leg.

In accordance with an embodiment, FIG. 1 is a drawing illustrating a power generating leg 100. Power generating leg 100 is configured to be coupled to a person's lower limb. Power generating leg 100 comprises a thigh link 103 and a shank link 105. A knee mechanism 107 is connected to thigh link 103 and shank link 105. Knee mechanism 107 is configured to allow flexion movements (in the direction of arrows 240) and extension movements (in the direction of arrows 241) between thigh link 103 and shank link 105. A torque generator 213 is configured to impose a torque that affects the movements of thigh link 103 and shank link 105 relative to each other. A power unit 215 is coupled to torque generator 213, and is configured to cause torque generator 213 to generate torque.

When power unit 215 operates in a power regeneration mode, power unit 215 is configured to cause torque generator 213 to generate a torque that opposes the angular velocity of thigh link 103 and shank link 105 relative to each other. In this power regeneration mode, power unit 215 further converts a portion of the power associated with the product of the generated torque and the angular velocity of shank link 105 and thigh link 103 relative to each other into electrical power to be stored in a storage device. In some embodiments, the storage device is located within power unit 215. In some embodiments, the storage device is external. In some embodiments, the converted electrical power is stored in a set of batteries. In some embodiments, the converted electrical power is stored in a set of capacitors.

In some embodiments, power unit 215 further operates in a power utilization mode. During this mode, power unit 215, using stored power, is configured to cause torque generator 213 to generate a torque. In some embodiments, a portion of the power used in the power utilization mode is the electrical power generated in the power regeneration mode.

In some embodiments, power unit 215 further operates in a power dissipation mode. During this mode, power unit 215 is configured to cause torque generator 213 to generate a torque that opposes the angular velocity of thigh link 103 and shank link 105 relative to each other. Power unit 215 also dissipates the power associated with the product of the torque and the angular velocity of thigh link 103 and shank link 105 relative to each other.

Figure 2:
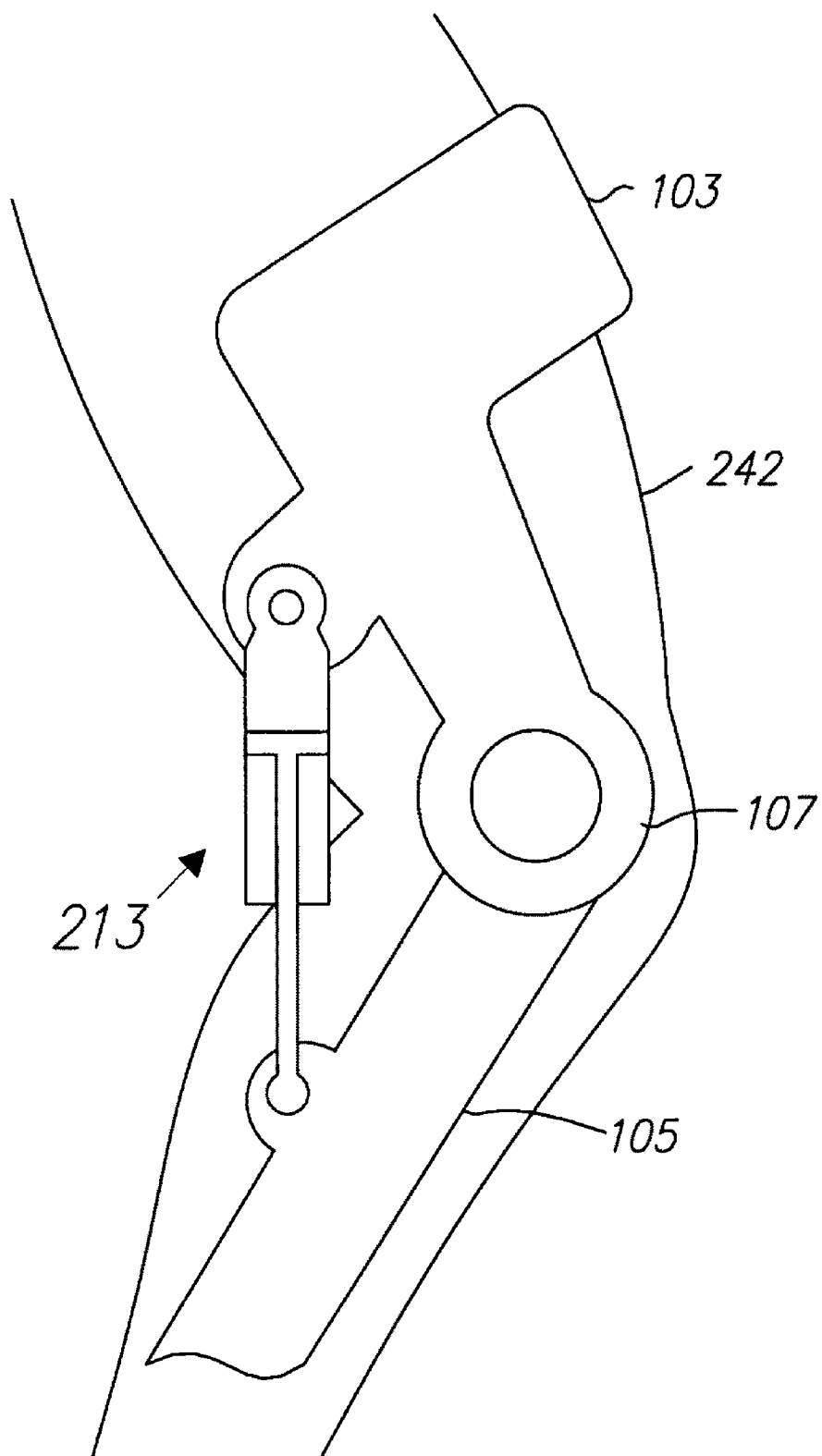
FIG. 2 is a side view of an exemplary embodiment of a power generating leg coupled to a person's lower limb.

In some embodiments, as shown in FIG. 2, knee mechanism 107 comprises at least one rotary joint. The rotary joint is configured to allow for rotary flexion and extension movements of thigh link 103 and shank link 105 relative to each other.

Figure 3:
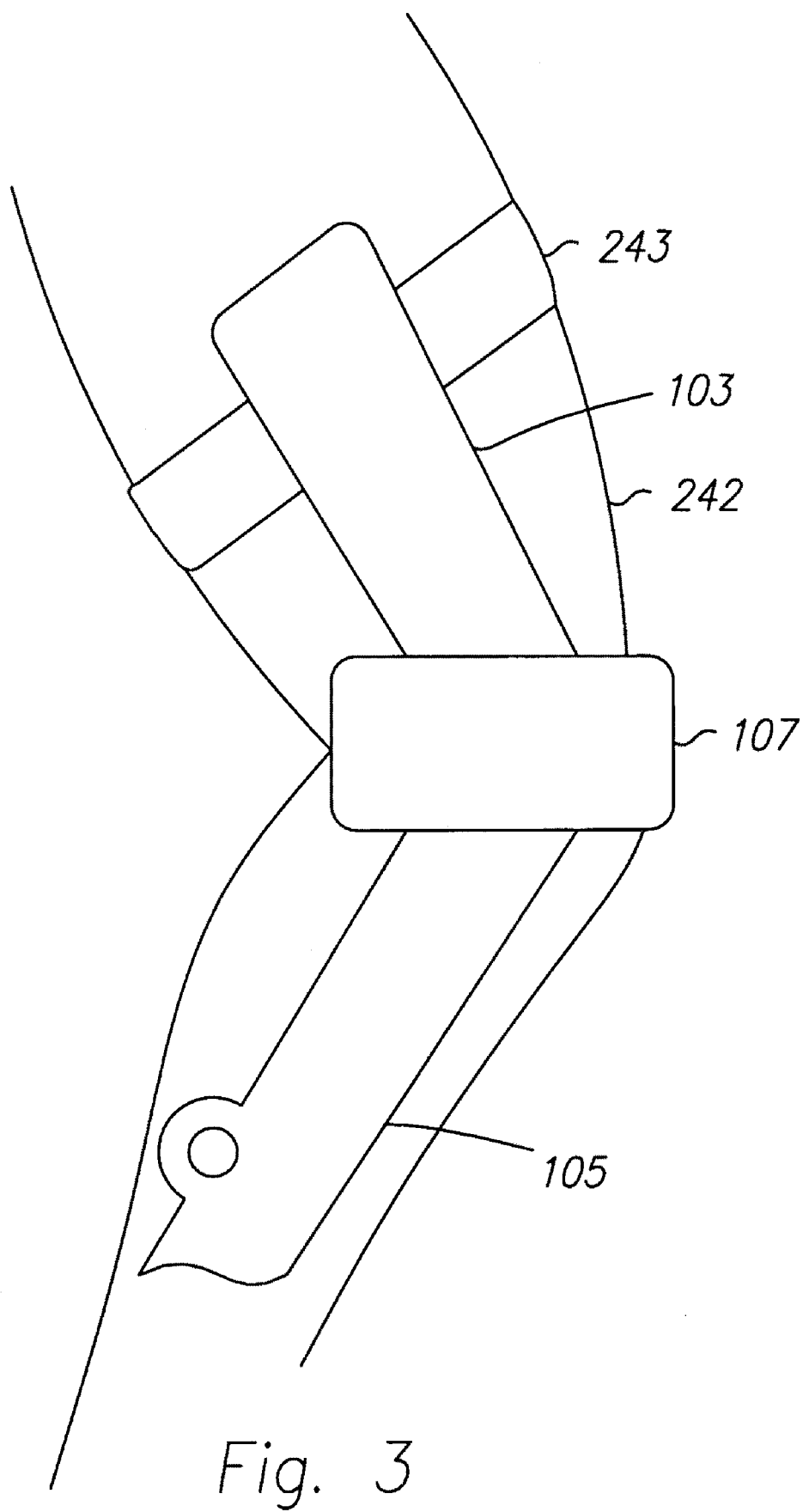
FIG. 3 is a side view of an exemplary embodiment of a power generating leg coupled to a person's lower limb.

In some embodiments, as shown in FIG. 2, thigh link 103 is in contact with a person's thigh 242 so it can be moved by the person's thigh. In some embodiments, thigh link 103 is connectable to a person's thigh. FIG. 3 shows an embodiment where power generating leg 100 comprises a thigh strap 243 connectable to a person's thigh 242 and causes thigh link 103 to move when the person's thigh moves. Torque generator 213 is not shown in FIG. 3 for clarity.

Figure 4:
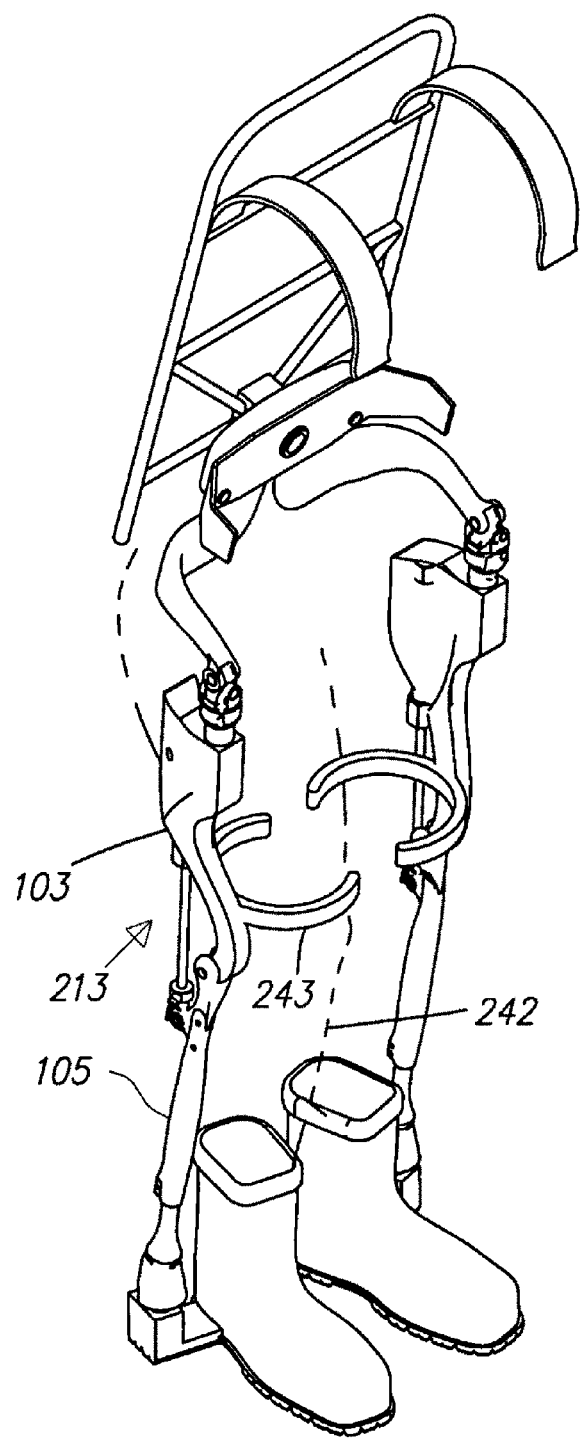
FIG. 4 is a perspective view of an exemplary embodiment of a power generating leg.

In some embodiments, thigh strap 243, among other components, comprises compliant materials wrapped around the person's thigh. Compliant materials comprise an element or combination of elements selected from a group consisting of fabric, textile, elastomer, rubber and velcro materials. In some embodiments, as shown in FIG. 4, thigh strap 243 comprises a bracket formed to partially embrace the person thigh.

Figure 5:
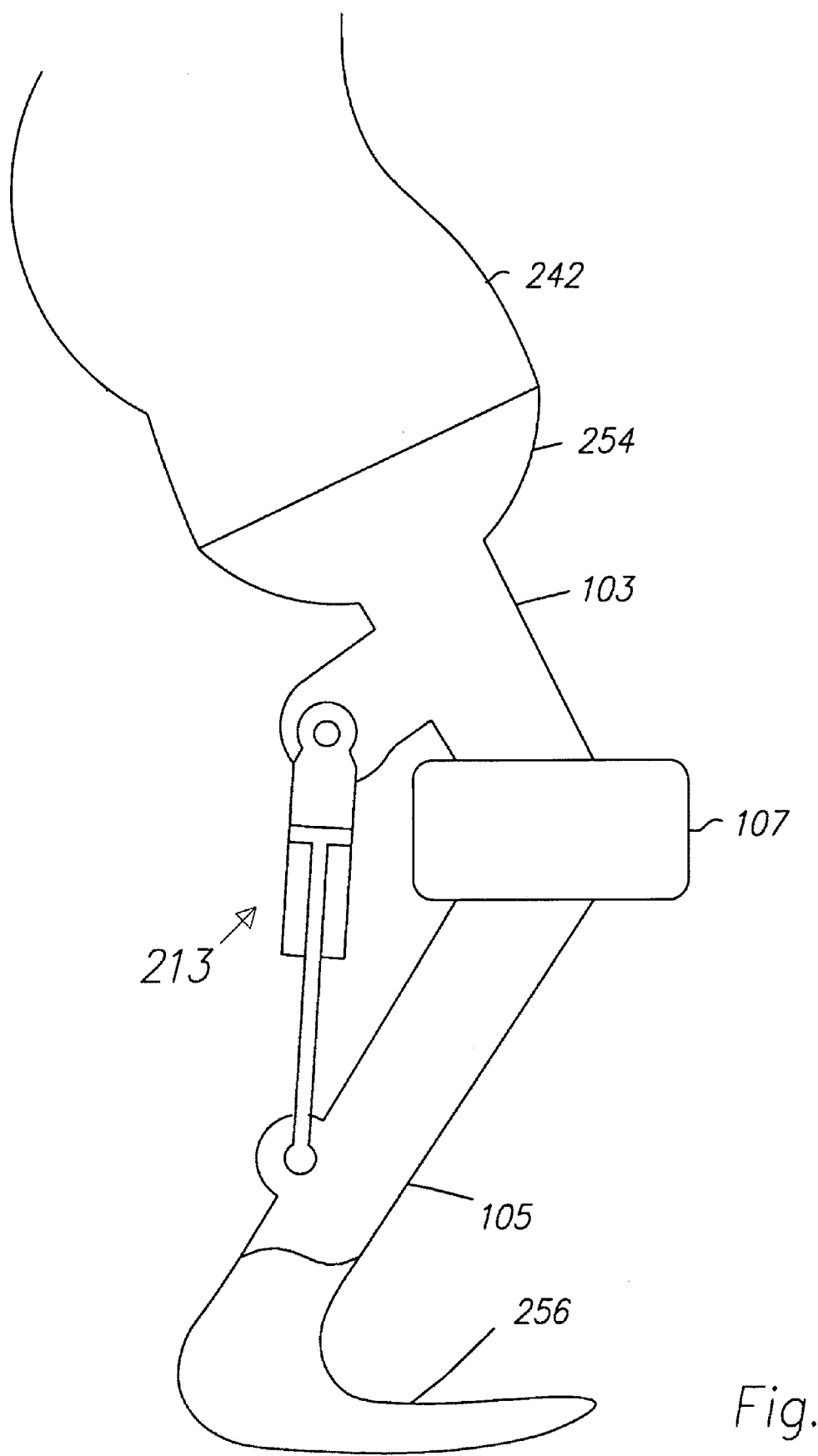
FIG. 5 is a side view of an exemplary embodiment of a power generating leg coupled to a person's lower limb that acts as a prosthetic leg.

In some embodiments, as shown in FIG. 5, power generating leg 100 acts as a prosthetic leg for above-knee amputees. In this case, thigh link 103 comprises a socket 254 attachable to an amputee's remaining thigh. Therefore, power generating leg 100 functions as an above knee prosthetic device. In some embodiments, power generating leg 100 includes an artificial foot 256.

Figure 6:
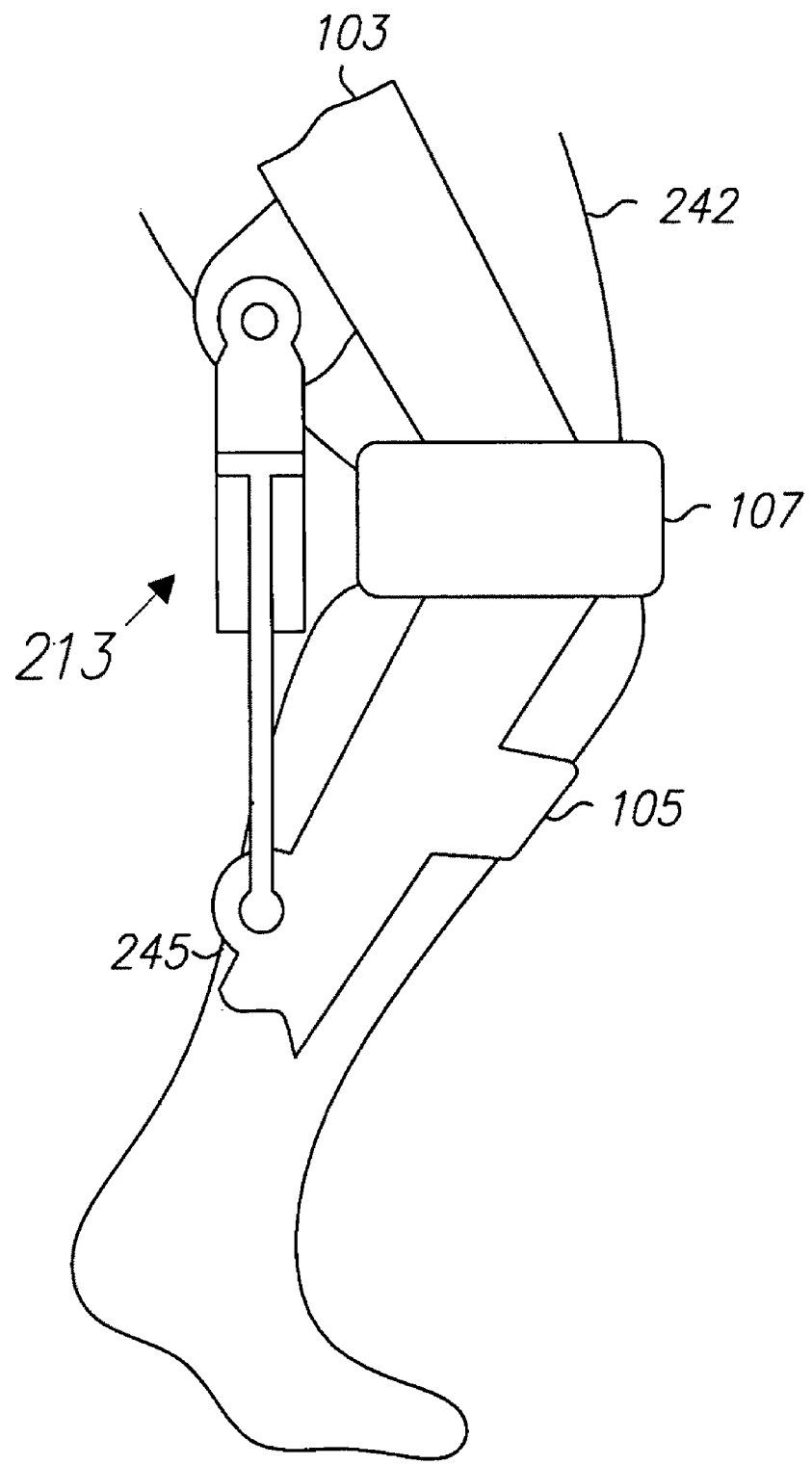
FIG. 6 is a side view of an exemplary embodiment of a power generating leg coupled to a person's lower limb.
Figure 7:
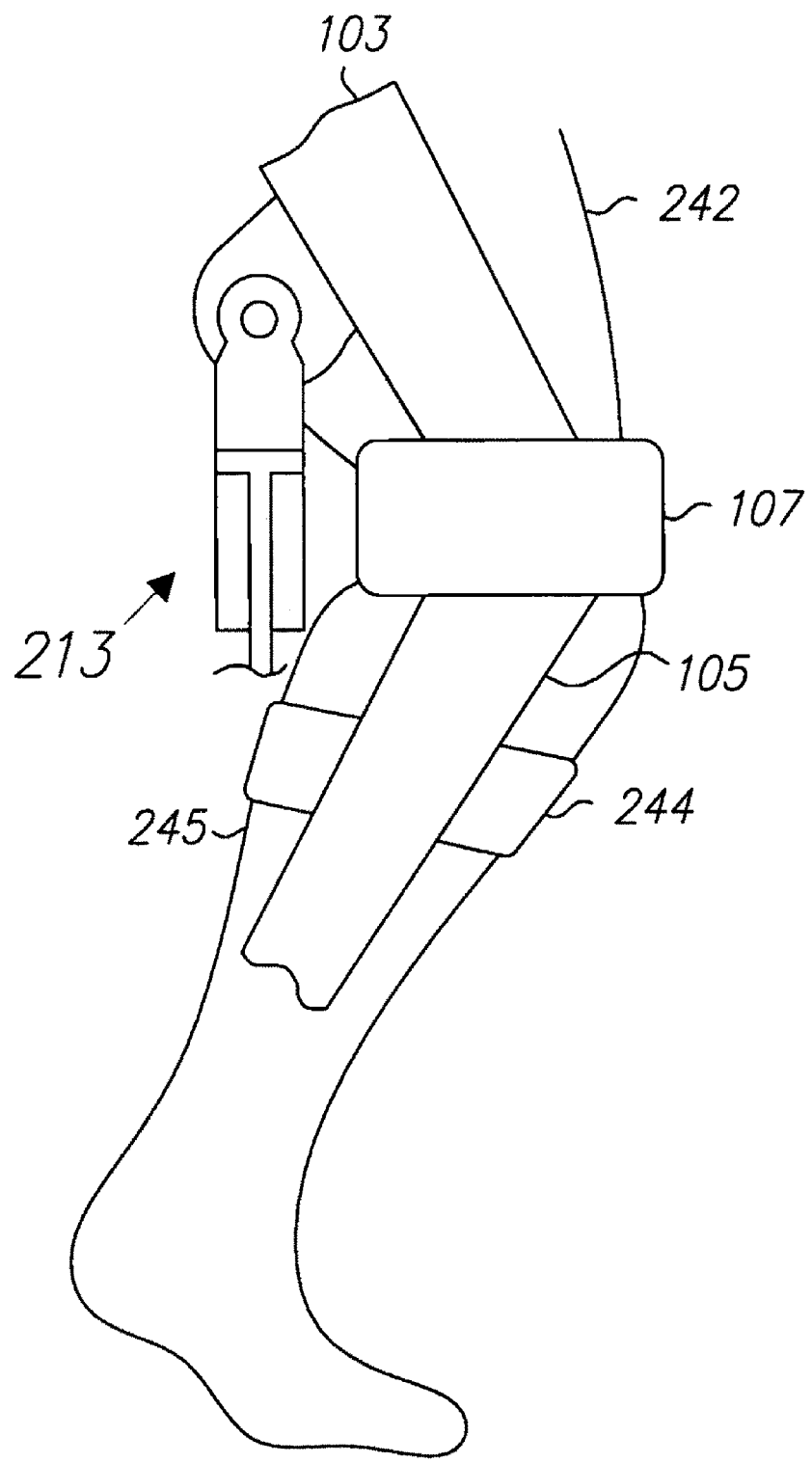
FIG. 7 is a side view of an exemplary embodiment of a power generating leg coupled to a person's lower limb.

According to an embodiment shown in FIG. 6, shank link 105 is configured to be in contact with a person's shank so it can be moved by the person's shank. In some embodiments, shank link 103 is configured to be connected to a person's shank. FIG. 7 shows an embodiment where power generating leg 100 comprises a shank strap 244 configured to be connected to a person's shank 245 and causes shank link 105 to move when the person's shank moves. Torque generator 213 is partially shown in FIG. 7 for clarity.

Figure 8:
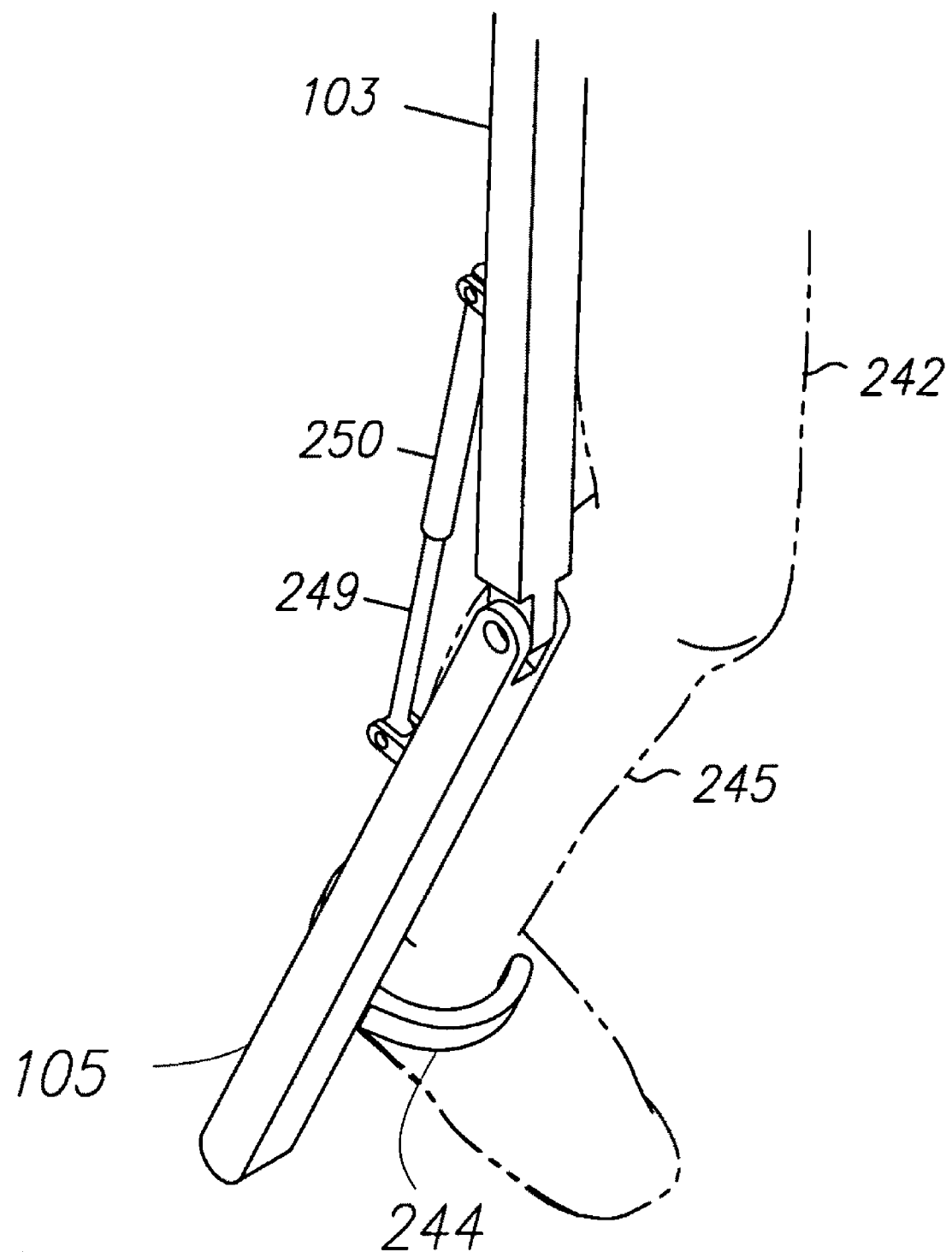
FIG. 8 is a side view of an exemplary embodiment of a power generating leg coupled to a person's lower limb.

In some embodiments, shank strap 244, among other components, comprises compliant materials wrapped around the person's shank 245. Compliant materials comprise an element or combination of elements selected from a group consisting of fabric, textile, elastomer, rubber and velcro materials. In some embodiments, as shown in FIG. 8, shank strap 244 comprises a bracket formed to partially embrace the person's shank 245.

In summary, power generating leg 100 can be an orthotic leg or a prosthetic leg. In some embodiments, power generating leg 100 is a leg of an exoskeleton as shown in FIG. 4.

Figure 9:
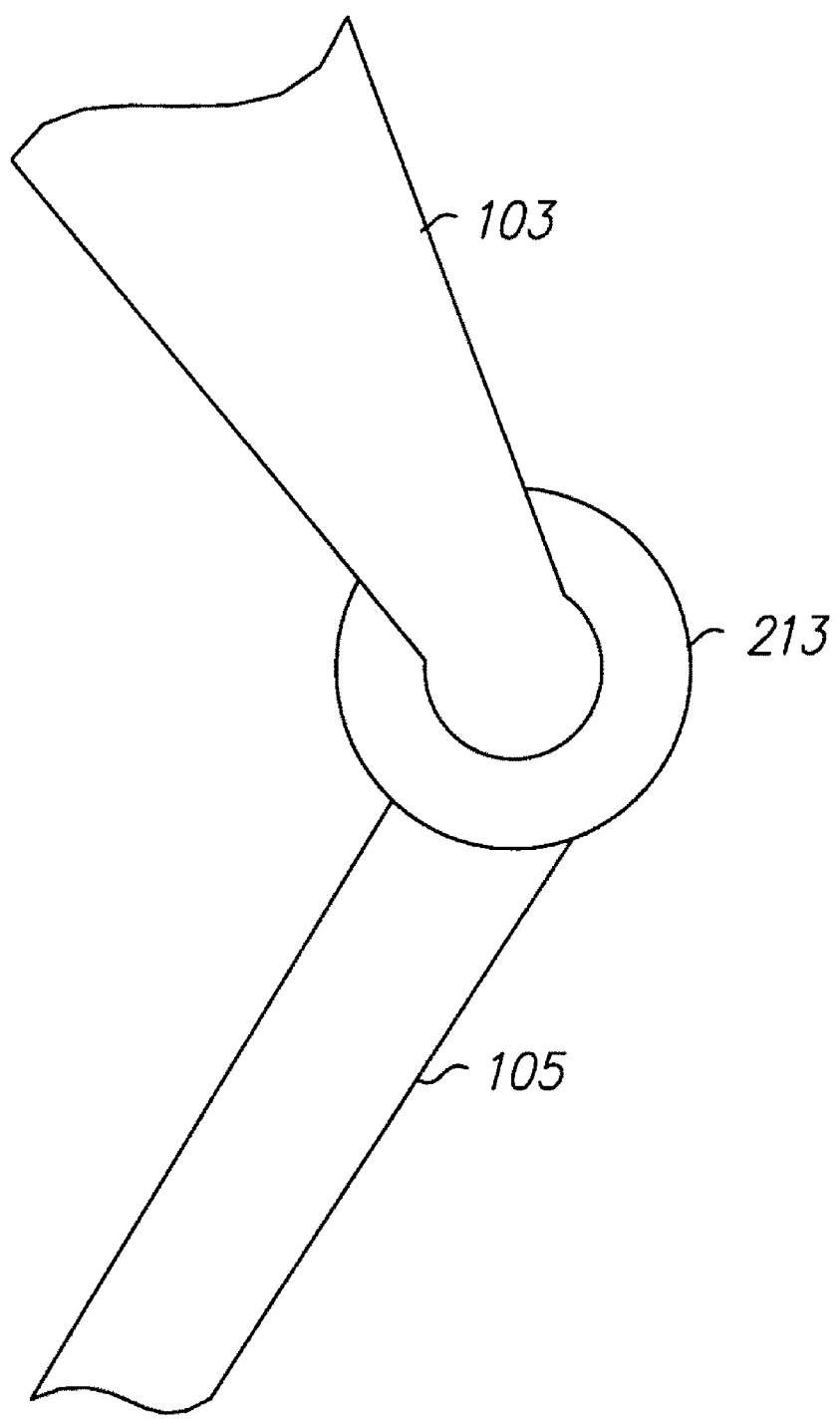
FIG. 9 is a side view of a portion of an exemplary embodiment of a power generating leg.

In some embodiments, as shown in FIG. 1, torque generator 213 comprises a hydraulic torque generator where a pressurized hydraulic fluid, by pushing against moving surfaces, generates torque. Examples of hydraulic torque generators 213 include, without limitation, linear hydraulic piston-cylinders and rotary hydraulic actuators where pressurized hydraulic fluid, by pushing against moving surfaces, generate force or torque. An illustration of a power generating leg 100 utilizing linear hydraulic piston-cylinder torque generator 213 is shown in FIG. 1, where piston 249 slides relative to cylinder 250. An illustration of a power generating device 100 utilizing a rotary hydraulic actuator is shown in FIG. 9. In some embodiments, as shown in FIG. 9, torque generator 213 is integrated into the construction of knee mechanism 107.

Figure 10:
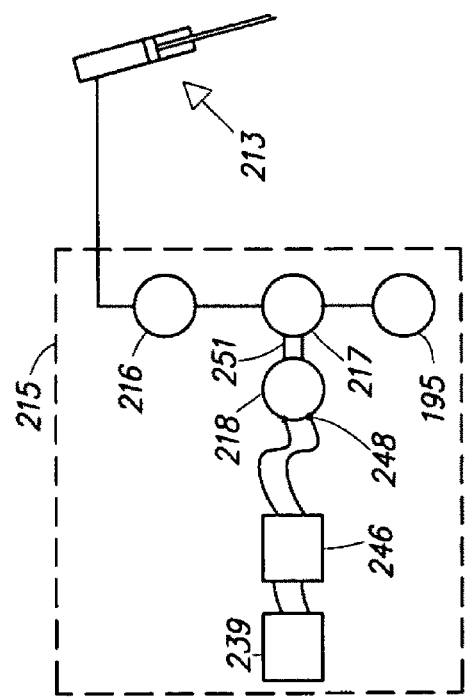
FIG. 10 is a block diagram of an exemplary embodiment of a power unit.

FIG. 10 shows an embodiment of power unit 215. Power unit 215 comprises a hydraulic motor 217 where its two hydraulic ports are connected to torque generator 213 and a fluid reservoir 195. Hydraulic reservoir 195 may be a separate reservoir as shown, or it may be the other cavity of the torque generating device 213. Hydraulic motor 217 is a device that converts hydraulic fluid flow into mechanical rotation of a rotating shaft 251.

An electric generator 218, capable of producing electric voltage on its terminals 248, is rotatably coupled to rotating shaft 251 of hydraulic motor 217. When power unit 215 is in power regeneration mode, electric generator 218 generates electric voltage on its terminals 248 when the hydraulic fluid flow between torque generator 213 and fluid reservoir 195 causes the rotor of hydraulic motor 217 to turn. The generated voltage on terminals 248 is a function of the angular velocity of thigh link 103 and shank link 105 relative to each other. When an electric current is allowed to pass through terminals 248 such that the product of current and the generated voltage indicates that electric power is generated, hydraulic motor 217 resists the fluid flow that is induced by the motion of thigh link 103 and shank link 105 relative to each other. This resistance to fluid flow causes torque generator 213 to impose a torque, which resists the motion of thigh link 103 and shank link 105 relative to each other. This torque is a function of the electric current that is flowing through terminals 248 of electric generator 218. By controlling the electric current that is flowing through terminals 248, one can control the torque generated by hydraulic torque generator 213.

When power unit 215 is in power regeneration mode, power unit 215 converts only a portion of the mechanical power associated with the product of the generated torque and the relative speed of thigh link 103 and shank link 105 into electric power. The rest of this power is converted into heat in such things as the motor winding and hydraulic fluid. In some embodiments, power unit 215 further comprises a battery charging unit 246 that charges at least one battery 239. In some embodiments, battery 239 is located outside power unit 215.

When power unit 215 is operating in power utilization mode, hydraulic motor 217 acts like a hydraulic pump and electric generator 218 acts like an electric motor. In operation, when power unit 215 is in power utilization mode, hydraulic motor 217 causes torque generator 213 to generate torque when an electric current passes through terminals 248 of electric generator 218. The generated torque in torque generator 213 is a function of the electric current passing through terminals 248. By controlling the electric current that is passing through terminals 248, one can control the torque generated by hydraulic torque generator 213. When hydraulic fluid flows between fluid reservoir 195 and torque generator 213, a portion of stored electrical power is converted into the mechanical power associated with the product of the generated torque and the relative speed of thigh link 103 and shank link 105 into electric power.

Examples of electric generator 218 include, without limitation, AC (alternating current) generators, brush-type DC (direct current) generators, brushless DC generators, electronically commutated motors (ECMs), and combinations thereof. Examples of hydraulic motor 217 include, without limitation, hydraulic gear motors, axial piston pumps, rotary piston pumps, vane type hydraulic motors and combinations thereof.

Figure 11:
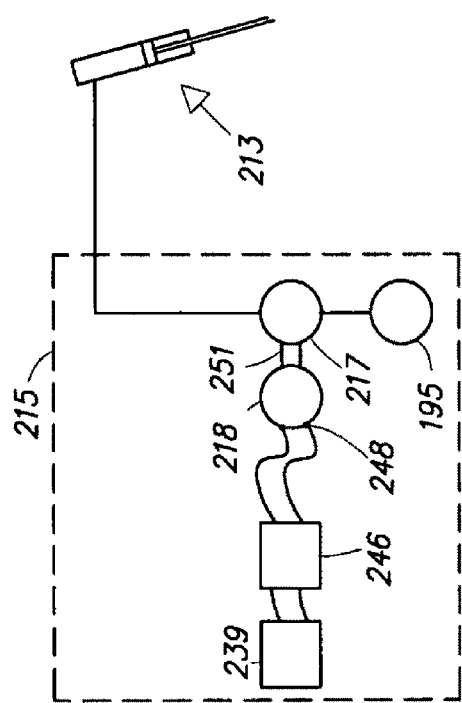
FIG. 11 is a block diagram of an exemplary embodiment of a power unit.

FIG. 11 shows another embodiment of power unit 215. This embodiment is similar to embodiment shown in FIG. 10 but a motor isolating valve 216 is located in series with hydraulic motor 217. The operation of this embodiment, when motor isolating valve 216 is in an open position, is similar to the operation of the embodiment of FIG. 10. When the motor isolating valve is in a closed position, no hydraulic flow is permitted and therefore thigh link 103 and shank link 105 cannot move relative to each other. This characteristic can be used during stance. Motor isolating valve 216 comprises any valve or combination of valves capable of performing the indicated functions. Examples of motor isolating valve 216 include, without limitation, flow control valve, pressure control valve, actuated needle valves, solenoid valves and on-off valve.

Figure 12:
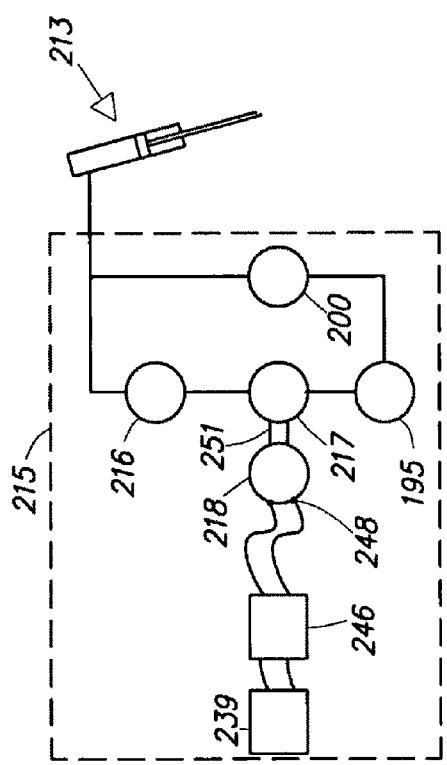
FIG. 12 is a block diagram of an exemplary embodiment of a power unit.

In some embodiments, as shown in FIG. 12, power unit 215 further comprises an actuated flow restricting valve 200 with adjustable orifice coupled to torque generator 213 and fluid reservoir 195 creating a second hydraulic path between torque generator 213 and fluid reservoir 195. When motor isolating valve 216 is in a closed position, actuated flow restricting valve 200 can be adjusted to allow proper resistance for the fluid flow between torque generator 213 and fluid reservoir 195. The amount of this resistance to fluid flow causes torque generator 213 to impose a resistive torque which resists the motion of thigh link 103 and shank link 105 relative to each other. This characteristic is used in power dissipation mode and can be used to damp the knee motion. Actuated flow restricting valve 200 comprises any valve or combination of valves capable of performing the indicated functions. Examples of actuated flow restricting valve 200 include, without limitation, flow control valve, pressure control valve, actuated needle valves, solenoid valves and on-off valve.

Figure 13:
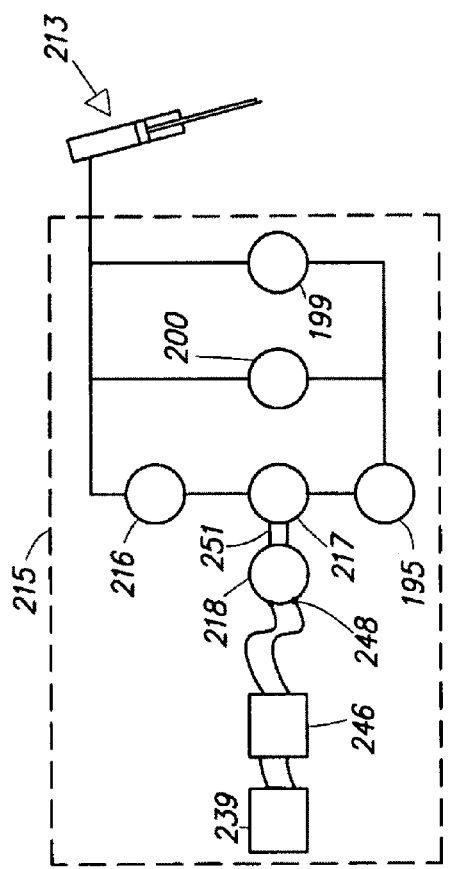
FIG. 13 is a block diagram of an exemplary embodiment of a power unit.

In some embodiments, as shown in FIG. 13, power unit 215 further comprises a check valve (one-way valve) 199 coupled to torque generator 213 and fluid reservoir 195 creating another hydraulic path between torque generator 213 and fluid reservoir 195. Check valve 199 allows for minimum resistance hydraulic flow from fluid reservoir 195 to torque generator 213 during extension movement of thigh link 103 and shank link 105 relative to each other at all times.

Figure 14:
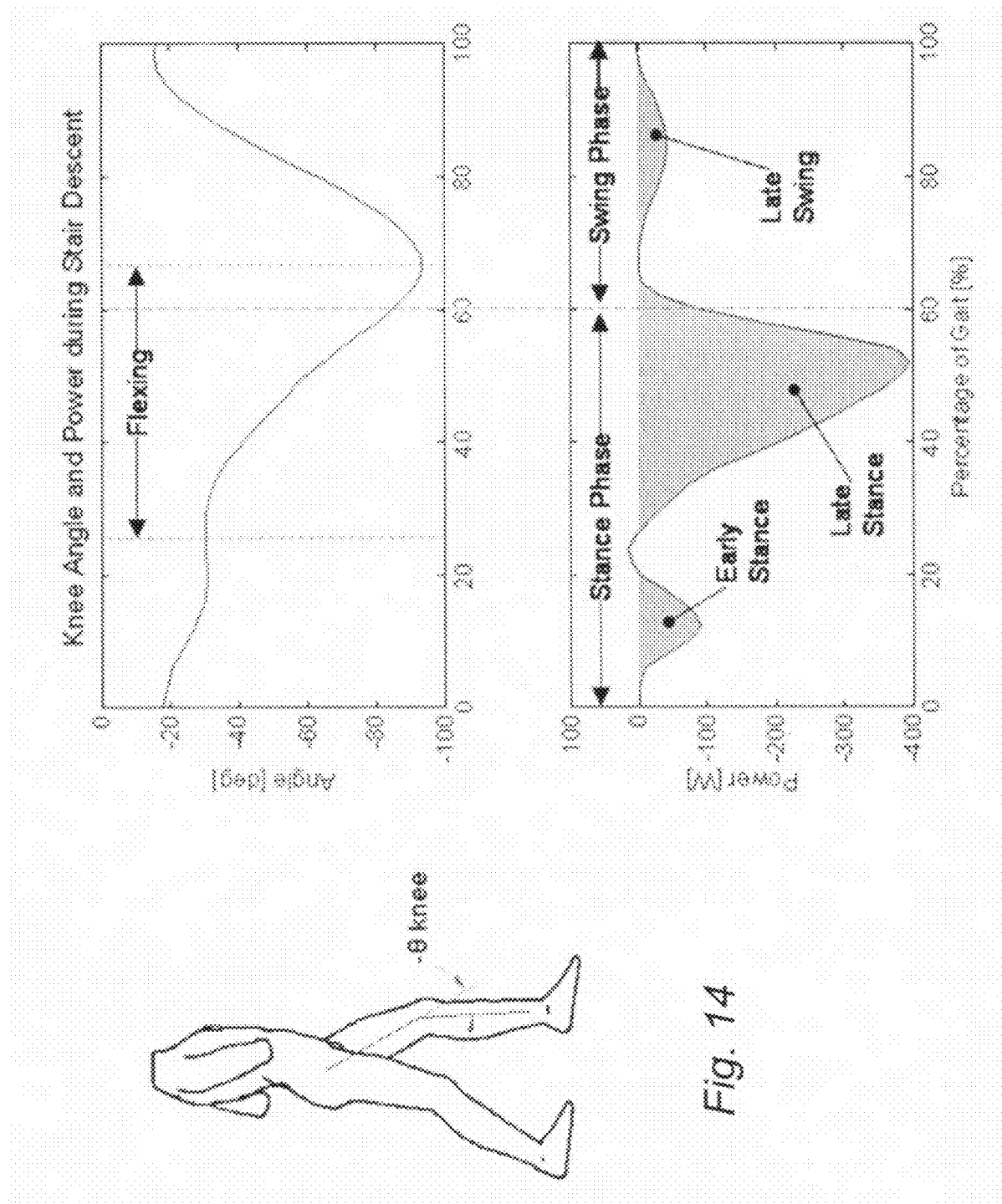
FIG. 14 is a graph depicting the knee power and the knee angle where a human is descending steps.

In operation, there are opportunities where power unit 215 moves into power regeneration mode and therefore power unit 215 converts a portion of the power associated with the product of the generated torque and the angular velocity of shank link 105 and thigh link 103 relative to each other into electrical power. FIG. 14 shows the knee angle and the knee power when a human is descending steps. Negative values for power identify the regions that have potential for power regeneration. A power regeneration region is identified where power regenerating leg 100 is in a stance phase and flexing. Stance phase is defined as a configuration where power regenerating leg 100 or the human leg it is connected to is on the ground. In some embodiments, power unit 215 is configured to operate in a power regeneration mode when power generating leg 100 is in a stance phase and is descending slopes and stairs. In some embodiments, power unit 215 is configured to operate in a power regeneration mode when said power generating leg 100 is in a stance phase and is flexing. In some embodiments, power unit 215 is configured to operate in a power regeneration mode when said power generating leg 100 is in a stance phase.

Figure 15:
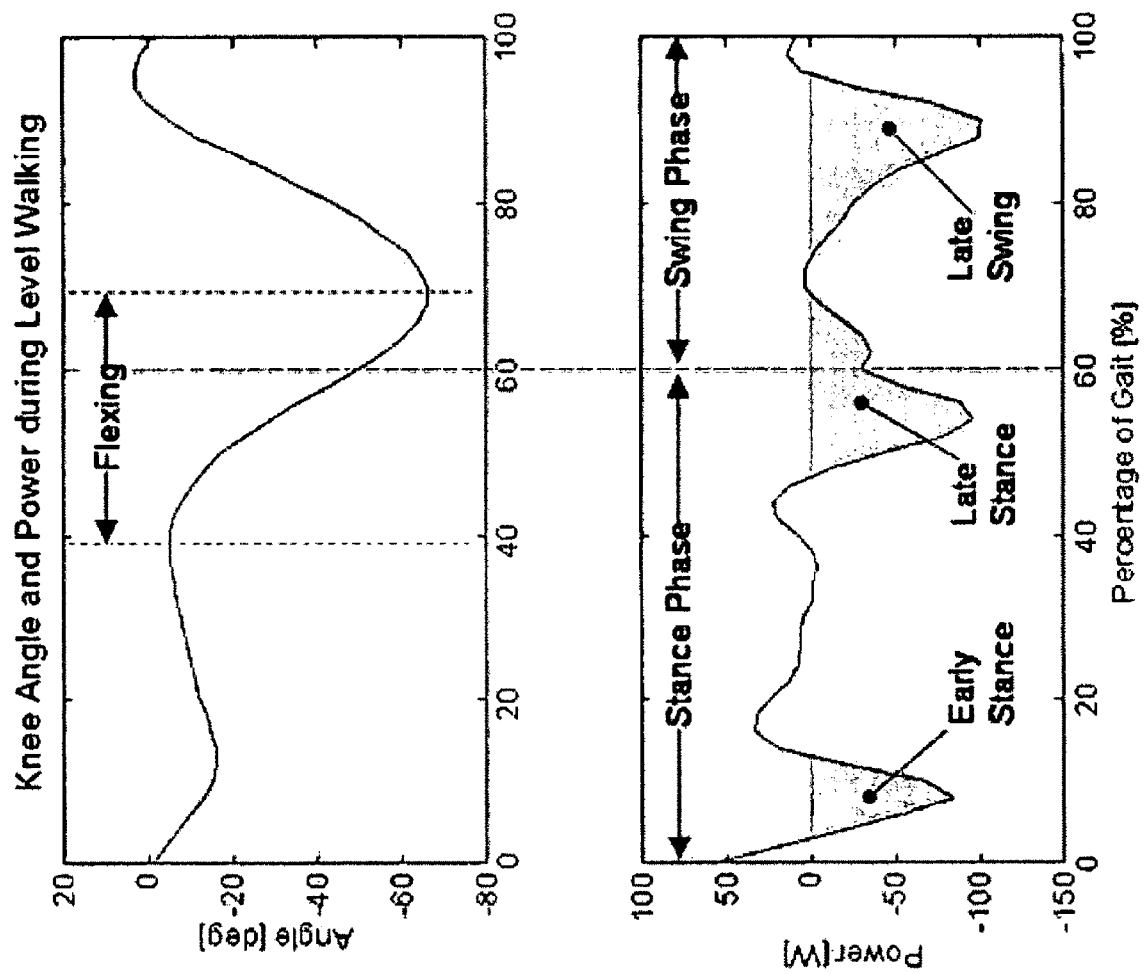
FIG. 15 is a graph depicting the knee torque and the knee angle where a human is walking on a level ground.

FIG. 15 shows the knee angle and the knee power when a human is walking on level grounds. Negative values for power identify the regions that have potential for power regeneration. In some embodiments, power unit 215 is configured to operate in power regeneration mode when power generating leg 100 is in a stance phase and is walking on level grounds. In some embodiments, power generating leg 100 is configured to operate in a power regeneration mode when power generating leg 100 is in a swing phase.

Figure 16:
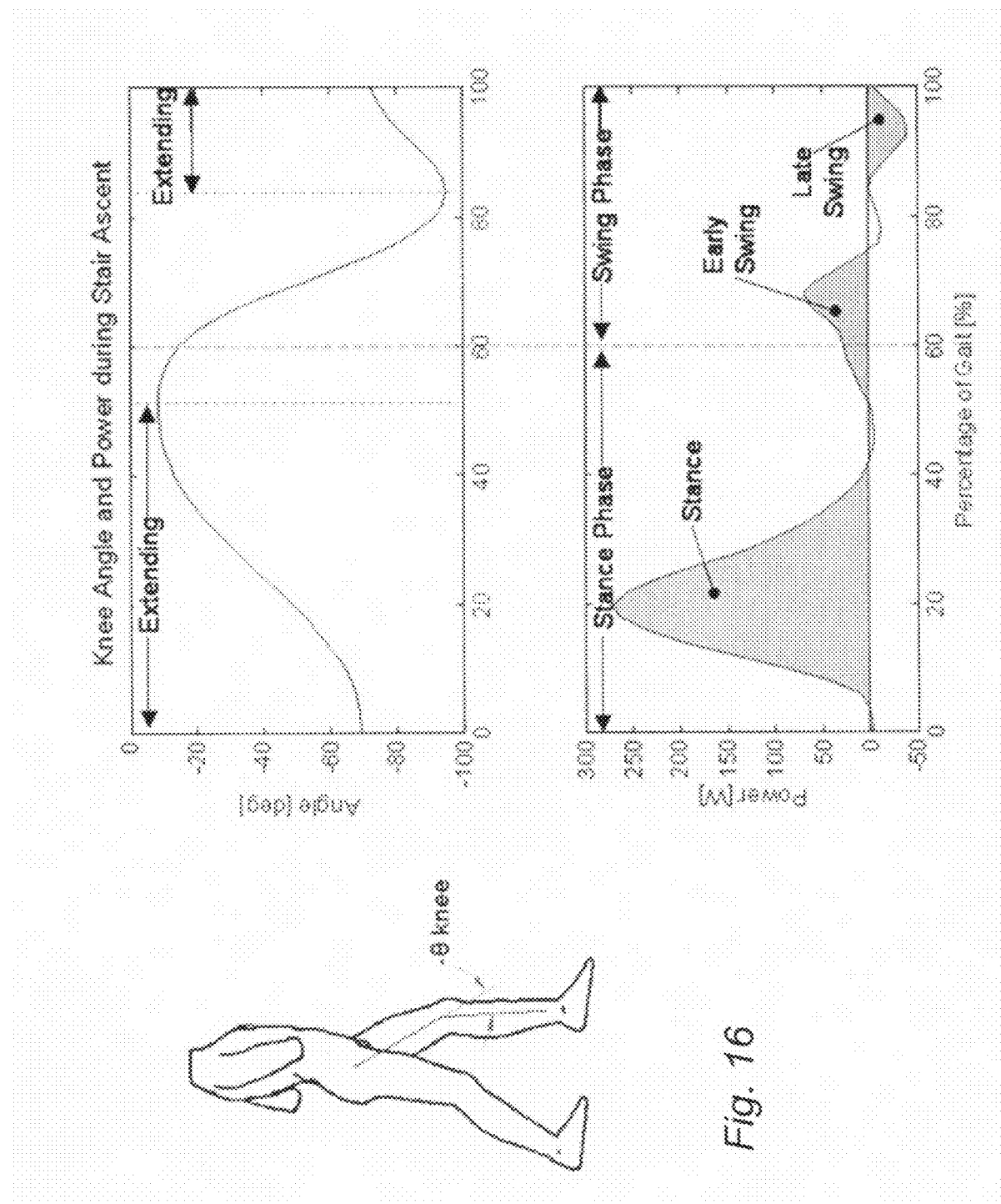
FIG. 16 shows the knee power and the knee angle where a human is ascending steps.

In operation, there are opportunities where power unit 215 moves into power utilization mode. FIG. 16 shows the knee torque and the knee angle when a human is ascending steps. Positive values for power identify the regions that have potential for power utilization. In some embodiments, power unit 215 is configured to operate in power utilization mode when power generating leg 100 is in a stance phase and is ascending slopes and stairs. In some embodiments, power unit 215 is configured to operate in power utilization mode when power generating leg 100 is in a stance phase and is extending.

Figure 17:
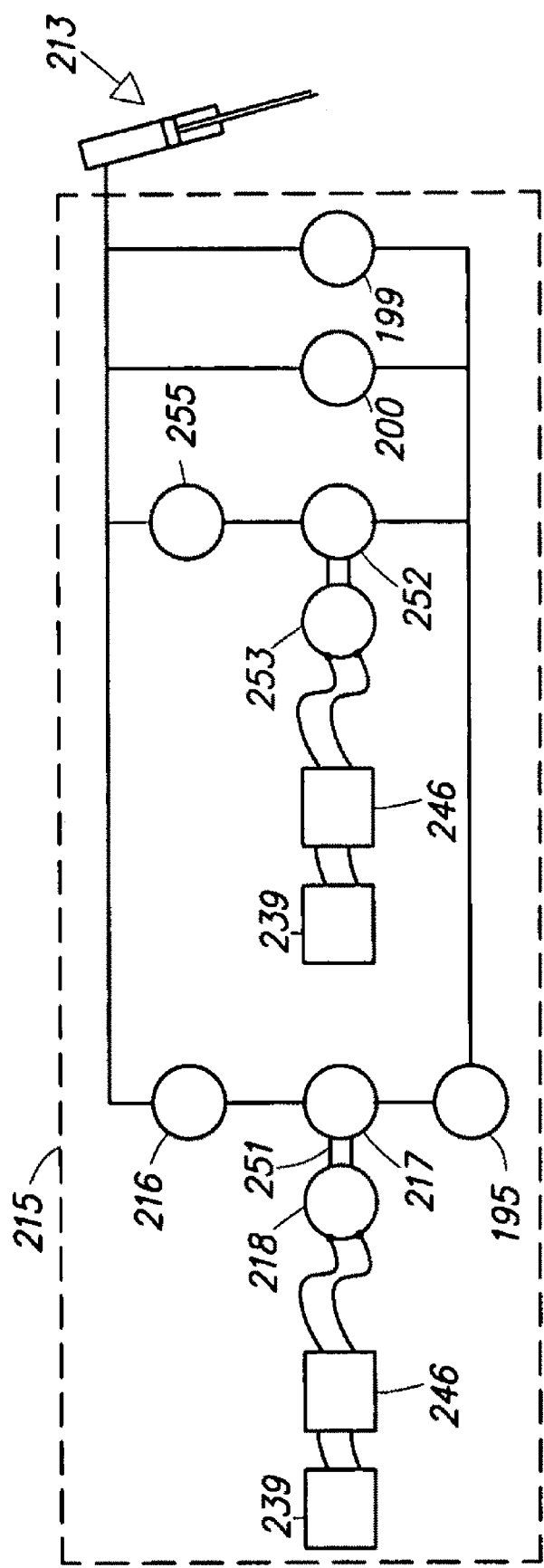
FIG. 17 is a block diagram of an exemplary embodiment of a power unit.

In some embodiments, power unit 215, as shown in FIG. 17, comprises two electric generators and hydraulic motors. Power unit 215 is coupled to hydraulic torque generator 213, and among other components, comprises a first hydraulic path between torque generator 213 and fluid reservoir 195 comprising a first hydraulic motor 217. Power unit 215 further comprises a second hydraulic path between torque generator 213 and fluid reservoir 195 comprising a second hydraulic motor 252. A first electric generator 218 is rotatably coupled to first hydraulic motor 217. A second electric generator 253 is rotatably coupled to second hydraulic motor 252. In operation, when power unit 215 is in a power regeneration mode, at least one of electric generators 218 and 253 generates an electric voltage when the hydraulic fluid flows from torque generator 213 to said reservoir 195. Motor isolating valves 216 and 255 are configured to select either hydraulic motor 217 or 252 for operation. These two isolating valves 216 and 255 can be replaced by a three way selector valve selecting between hydraulic motor 217 or 252. Power unit 215 further comprises a battery charging unit 246 that charges at least one battery 239.

In some embodiments, first electric generator 218 is used in a power regeneration mode when power generating leg 100 is in a stance phase and descending a stair or a slope. In this case, motor isolating valve 255 is closed and stops the fluid flow to second hydraulic motor 252 while motor isolating valve 216 is open and allows for the fluid flow to first hydraulic motor 217. In such embodiments, first electric generator 218 is used as an electric motor in a power utilization mode when power generating leg 100 is in a stance and ascending a stair or a slope.

In some embodiments, second electric generator 253 is used in a power regeneration mode when power generating leg 100 is in a stance phase and walking on level ground. In this case, motor isolating valve 216 is closed and stops the fluid flow to first hydraulic motor 217, while motor isolating valve 255 is open and allows for the fluid flow to second hydraulic motor 252. In such embodiments, second electric generator 253 may be used as an electric motor in a power utilization mode when power generating leg 100 is in a swing phase.

In some embodiments, power unit 215 further comprises a third hydraulic path including a flow restricting valve 200. In operation, flow restricting valve 200 is used to create controllable resistance to fluid flow. This characteristic is used in power dissipation mode and can be used to damp the knee motion.

In some embodiments, power unit 215 further comprises a forth hydraulic path including a one way valve 199. In operation, one way valve 199 allows for minimum resistance flow from said reservoir 195 to torque generator 213 at all times.

Figure 18:
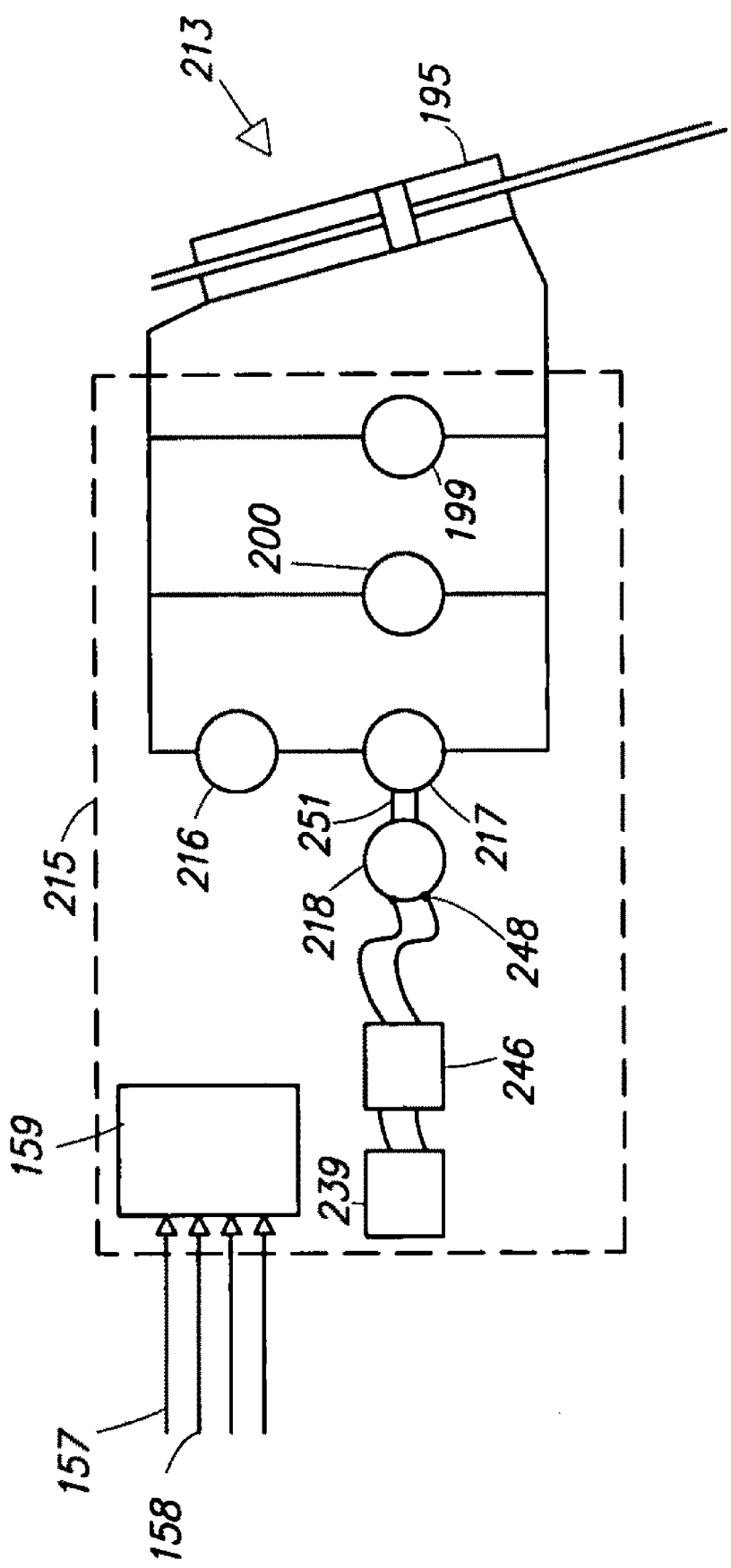
FIG. 18 is a block diagram of an exemplary embodiment of a power unit.

In some embodiments, as shown in FIG. 18, if torque generator 213 is a rotary hydraulic actuator or a double acting, double rodded hydraulic cylinder, then hydraulic reservoir 195 may be the other cavity of torque generator 213.

In some embodiments, power generating leg 100, among other sensors, comprises at least one stance sensor. Stance sensor produces a stance signal 157. Stance signal 157 identifies if power generating leg 100 is in a stance phase or in a swing phase. In some embodiments, stance signal 157 represents the magnitude of the ground reaction force to power generating leg 100. During swing phase, stance signal 157 will detect a small or zero magnitude for ground reaction force. Stance sensor comprises an element or combination of elements selected from a group consisting of force sensor, pressure sensor, and switches capable of performing the indicated functions.

In some embodiments, power generating leg 100, among other sensor, comprises at least one knee angle sensor. Knee angle sensor produces a knee angle signal 158. Knee angle signal 158 identifies the angle between shank link 105 and thigh link 103. Knee angle sensor comprises an element or combination of elements selected from a group consisting of encoder; revolver, potentiometer; LVDT, and inclinometer capable of performing the indicated functions.

In some embodiments, as shown in FIG. 18, power unit 215 further comprises a signal processor 159 is configured to generate command signals for various components of power unit 215 to control power unit 215. In some embodiments, signal processor 159 receives stance signal 157. In some embodiments, signal processor 159 receives knee angle signal 158. Signal processor 159 comprises an element or combination of elements selected from a group consisting of analog devices; analog computation modules; digital devices including, without limitation, small-, medium-, and large-scale integrated circuits, application specific integrated circuits, programmable gate arrays, and programmable logic arrays; and digital computation modules including, without limitation, microcomputers, microprocessors, microcontrollers, and programmable logic controllers. In some embodiments, signal processor 159 comprises an element or combination of elements selected from a group consisting of electromechanical relays or MOSFET switches. Signal processor 159 may be located inside or outside of power unit 215.

There are many control algorithms by which signal processor 159 could control power unit 215. In some embodiments, when power generating leg 100 is descending a slope or stairs and is in a stance phase, signal processor 159 generates command signals so power unit 215 goes into power regeneration mode. A knee angle near 180° at the beginning of stance and a smaller angle at the end of stance may represent the situation where power generating leg 100 is descending a slope or stairs. See, U.S. patent application Ser. No. 10/976,652, titled LOWER EXTREMITY ENHANCER, filed on Oct. 29, 2004; U.S. patent application Ser. No. 11/335,392, titled LOWER EXTREMITY EXOSKELETON, filed on Jan. 18, 2006; and U.S. patent application Ser. No. 11/404,719, titled SEMI-POWERED LOWER EXTREMITY EXOSKELETON, filed on Apr. 13, 2006; all of which are incorporated herein by reference in their entireties for all purposes.

In some embodiments, when power generating leg 100 is ascending a slope or stairs and is in a stance phase, signal processor 159 generates command signals so power unit 215 operates in the power utilization mode. This mode aids the wearer in climbing slopes and stairs. A small knee angle at the beginning of stance phase may represent the situation where power generating leg 100 is ascending a slope or stairs.

In some embodiments, when power generating leg 100 is walking on level ground and is in stance phase, signal processor generates command signals so power unit 215 operates in the power dissipation mode or power regeneration mode depending on operator preference. A large knee angle close to 180° degrees at the beginning of stance phase which does not change for a long period of stance may represent the situation where power generating leg 100 is walking on level ground.

In some embodiments, when power generating leg 100 is in a swing phase, signal processor 159 generates command signals so power unit 215 goes into power dissipation mode or power utilization mode to assist the swinging depending on operator preference.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

We claim:

1. A power generating leg, configured to be coupled to a person's lower limb, comprising:
    a thigh link;
    a shank link;
    a knee mechanism connected to said thigh link and said shank link, and configured to allow flexion and extension movements of said thigh link and said shank link relative to each other;
    a hydraulic torque generator configured to generate torque between said shank link and said thigh link; and
    a power unit configured to operate in both a power utilization mode and a power dissipating mode, said power unit including a first hydraulic path between a fluid reservoir and the hydraulic torque generator having a hydraulic motor rotatably coupled to an electric generator and a motor isolating valve connected in series, and a second hydraulic path between the fluid reservoir and the hydraulic torque generator including an actuated flow restricting valve;
    wherein when said power unit is in a power utilization mode, said motor isolating valve is in an open position and said hydraulic motor is powered by the electric generator and actuates the hydraulic torque generator to create a torque between the thigh link and the shank link; and
    wherein when said power unit is in a power dissipation mode, said motor isolating valve is in a closed position and said actuated flow restricting valve restricts fluid flow between the hydraulic torque generator and the fluid reservoir and causes the hydraulic torque generator to resist motion of the thigh link and shank link with respect to one another.

2. The power generating leg of claim 1 further comprising:
    a storage device,
    wherein the power unit is configured to operate in the power utilization mode, the power dissipating mode or a power regeneration mode, and
    wherein when said power unit is in a power regeneration mode, said power unit causes said torque generator to generate a torque that opposes an angular velocity of said thigh link and said shank link relative to each other and said power unit converts a portion of the power associated with the product of said torque and said angular velocity of said shank link and thigh link relative to each other into electrical power to be stored in a storage device.

3. The power generating leg of claim 2 wherein when said motor isolating valve is in an open position and when said power unit is in said power regeneration mode, said hydraulic motor resists the hydraulic flow induced by the motion of said hydraulic torque generator and an electric current passes through the terminals of said electric generator indicating that electric power is being generated by said electric generator.

4. The power generating leg of claim 2 wherein when said motor isolating valve is in an open position and said power unit is in said power regeneration mode, said torque generator generates a torque that opposes the velocity of said torque generator and an electric current passes through the terminals of said electric generator indicating that electric power is being generated by said electric generator.

5. The power generating leg of claim 4 wherein said power unit is configured to operate into a in the power regeneration mode when said power generating leg is in a stance phase.

6. The power generating leg of claim 4 wherein said power unit is configured to operate in the power regeneration mode when said power generating leg is in a stance phase and is flexing.

7. The power generating leg of claim 4 wherein said power unit is configured to operate in the power regeneration mode when said power generating leg is in a stance phase and is descending slopes and stairs.

8. The power generating leg of claim 4 wherein said power unit is configured to operate in the power regeneration mode when said power generating leg is in a stance phase and is walking on level grounds.

9. The power generating leg of claim 4 wherein said power unit is configured to operate in the power regeneration mode when said power generating leg is in a swing phase.

10. The power generating leg of claim 2, further comprising a third hydraulic path including a second electric generator rotatably coupled to a second hydraulic motor; and
    wherein when said power unit is in said power regeneration mode, at least one of said first or second hydraulic motors resists the hydraulic flow induced by the motion of said hydraulic torque generator and an electric current passes through the terminals of the corresponding first or second electric generator such that electric power is generated by said first or second electric generator.

11. The power generating leg of claim 10 wherein said third hydraulic path further comprises a motor isolating valve located in series with said second hydraulic motor.

12. The power generating leg of claim 10 wherein said power unit further comprises a fourth hydraulic path between said torque generator and said reservoir, said fourth hydraulic path comprising a one way valve allowing for minimum resistance flow from said reservoir to said torque generator at all times.

13. The power generating leg of claim 10 wherein said torque generator is coupled to another knee mechanism of another power generating leg.

14. The power generating leg of claim 10 wherein said reservoir comprises a cavity on the opposite side of a piston or vane of said hydraulic torque generator.

15. The power generating leg of claim 10 wherein said torque generator is coupled to the knee mechanism of a robotic exoskeleton.

16. The power generating leg of claim 15 wherein said torque generator is a hydraulic cylinder.

17. The power generating leg of claim 15 wherein said first electric generator is used in the power regeneration mode when said power generating leg is in stance phase and descending a stair or slope.

18. The power generating leg of claim 15 wherein said second electric generator is used in the power regeneration mode when said power generating leg is walking on level ground.

19. The power generating leg of claim 15 wherein said first electric generator is used as an electric motor in the power utilization mode when said power generating leg is in a stance phase and ascending a stair or slope.

20. The power generating leg of claim 15 wherein: said first electric generator is used in the power regeneration mode when said power generating leg is in a stance phase and descending a stair or slope and is used as an electric motor in the power utilization mode when said power generating leg is in a stance phase and ascending a stair or slope; and said second electric generator is used in the power regeneration mode when said power generating leg is walking on level ground.

21. The power generating leg of claim 1 wherein said storage device is one or more capacitors.

22. The power generating leg of claim 1 wherein said knee mechanism comprises it least one rotary joint and allows for rotary flexion and extension movements of said thigh link and said shank link relative to each other.

23. The power generating leg of claim 1 wherein said thigh link is configurable to be in contact with a person's thigh so it can be moved by said person's thigh.

24. The power generating leg of claim 1 wherein said thigh link is configurable to be connected to a person's thigh.

25. The power generating leg of claim 1 wherein said power generating leg comprises a thigh strap configurable to be connected to a person's thigh and causes said thigh link to move when said person's thigh moves.

26. The power generating leg of claim 25 wherein said thigh strap comprises compliant materials wrapped around said person's thigh.

27. The power generating leg of claim 25 wherein said thigh strap comprises a bracket formed to partially embrace said person's thigh.

28. The power generating leg of claim 1 wherein said shank link is configurable to be in contact with said person's shank so it can be moved by said person's shank.

29. The power generating leg of claim 1 wherein said shank link is configurable to be connected to a person's shank.

30. The power generating leg of claim 1 wherein said power generating leg comprises a shank strap configurable to be connected to a person's shank and causes said shank link to move when said person's shank moves.

31. The power generating leg of claim 30 wherein said shank strap comprises compliant materials wrapped around said person's shank.

32. The power generating leg of claim 30 wherein said shank strap comprises a bracket formed to partially embrace said person's shank.

33. The power generating leg of claim 1 wherein said thigh link comprises a socket configurable to be attached to an amputee's remaining thigh and therefore said power generating leg functions as an above knee prosthetic device.

34. The power generating leg of claim 33 wherein said shank link further comprises an artificial foot.

35. The power generating leg of claim 1 wherein said hydraulic torque generator is a hydraulic piston and cylinder, wherein said piston slides relative to said cylinder.

36. The power generating leg of claim 1 wherein said hydraulic torque generator is a rotary hydraulic actuator.

37. The power generating leg of claim 1 wherein said electric generator comprises an element or combination of elements selected from a group consisting of AC generators, brush-type DC generators, brushless DC generators, electronically commutated motors, and combinations thereof.

38. The power generating leg of claim 1 wherein said fluid reservoir comprises a cavity on the opposite side of a piston or vane of said hydraulic torque generator.

39. The power generating leg of claim 1 where said power unit further comprises a one-way valve coupled to said torque generator and said fluid reservoir creating a third hydraulic path between said hydraulic torque generator and said fluid reservoir providing minimum resistance hydraulic flow from said fluid reservoir to said torque generator at all times.

40. The power generating leg of claim 1 wherein said power unit is configured to operate in the power utilization mode when said power generating leg is in a stance phase and is extending.

41. The power generating leg of claim 1 wherein said power unit is configured to operate in the power utilization mode when said power generating leg is in a stance phase and is ascending slopes and stairs.

42. The power generating leg of claim 1 wherein said power unit comprises a signal processor.

43. The power generating leg of claim 42 wherein said power generating leg comprises at least one knee angle sensor, wherein said knee angle sensor produces a knee angle signal representing the angle between said shank link and said thigh link.

44. The power generating leg of claim 43 wherein said signal processor generates command signals for components of said power unit from said knee angle signal.

45. The power generating leg of claim 42 wherein said power generating leg comprises at least a stance sensor, wherein said stance sensor produces a stance signal identifying if said power generating leg is in a stance phase or in a swing phase.

46. The power generating leg of claim 45 wherein said signal processor generates command signals for components of said power unit from said stance signal.

47. The power generating leg of claim 42 wherein said signal processor comprises an element or combination of elements selected from a group consisting of analog devices; analog computation modules; digital devices including, without limitation, small-, medium-, and large-scale integrated circuits, application specific integrated circuits, programmable gate arrays, and programmable logic arrays; and digital computation modules including, without limitation, microcomputers, microprocessors, microcontrollers, and programmable logic controllers.

48. The power generating leg of claim 42 wherein said signal processor comprises an element or combination of elements selected from a group consisting of electromechanical relays or metal oxide semiconductor field effect transistors switches.

49. The power generating leg of claim 1, wherein the flow restrictive valve is adjustable to allow a desired resistance of the fluid flow between the torque generator and the fluid reservoir.

50. A power generating prosthetic leg, comprising:
a thigh link configured to be coupled to an above-knee amputee's remaining limb;
a shank link;
a knee mechanism connected to said thigh link and said shank link, and
configured to allow flexion and extension movements of said thigh link and said shank link relative to each other;
a hydraulic torque generator configured to generate torque between said shank link and said thigh link; and
a power unit configured to operate in both a power utilization mode and a power dissipating mode, said power unit including a first hydraulic path between a fluid reservoir and the hydraulic torque generator having a hydraulic motor rotatably coupled to an electric generator and a motor isolating valve connected in series, and a second hydraulic path between the fluid reservoir and the hydraulic torque generator including an actuated flow restricting valve;
wherein when said power unit is in a power utilization mode, said motor isolating valve is in an open position and say hydraulic motor is powered by the electric generator and actuates the hydraulic torque generator to create a torque between the thigh link and the shank link; and
wherein when said power unit is in a power dissipation mode, said motor isolating valve is in a closed position and said actuated flow restricting valve restricts fluid flow between the hydraulic torque generator and the fluid reservoir and causes the hydraulic torque generator to resist motion of the thigh link and shank link with respect to one another.

51. A method of using an artificial leg comprising:
coupling a power generating leg to a person's lower limb, said power generating leg comprising: a thigh link; a shank link; a knee mechanism connected to said thigh link and said shank link, and configured to allow flexion and extension movements of said thigh link and said shank link relative to each other; a hydraulic torque generator configured to generate torque between said shank link and said thigh link; and a power unit coupled to said hydraulic torque generator, and configured to cause said hydraulic torque generator to generate torque, the power unit including a fluid reservoir in fluid communication with a hydraulic motor and the hydraulic torque generator; and
operating said power unit in a power regeneration mode, wherein when said power unit is in said power regeneration mode, and hydraulic fluid flows between the hydraulic torque generator and the fluid reservoir to cause the hydraulic motor to turn, a voltage is generated as a function of an angular velocity of the thigh link and shank link relative to each other, said power unit causes said torque generator to generate a torque that opposes the angular velocity of said thigh link and said shank link relative to each other and said power unit converts a portion of the power associated with the product of said torque and said angular velocity of said shank link and thigh link relative to each other into electrical power to be stored in a storage device.

52. The method of claim 51, wherein the power unit further comprises a motor isolating valve connected in series with the hydraulic motor in a first hydraulic path between the fluid reservoir and the hydraulic actuator, the method further comprising:
operating said power unit in a power utilization mode, wherein said motor isolating valve is in an open position and said hydraulic motor is powered by the electric generator and actuates the hydraulic torque generator to create a torque between the thigh link and the shank link.

53. The method of claim 52, wherein the power unit further comprises an actuated flow restricting valve in a second hydraulic path between the torque generator and the fluid reservoir, the method further comprising:
operating said power unit in a power dissipation mode, wherein said motor isolating valve is in a closed position and said actuated flow restricting valve resists motion of hydraulic fluid between the hydraulic torque generator and said fluid reservoir to resist the motion of the shank link with respect to the thigh link.

54. The method of claim 53, further comprising:
selecting a preference for operating the power generating leg in a power dissipation mode or a power regeneration mode;
sensing that the power generating leg is in a stance phase and is on level ground; and
signaling the power unit to operate in one of the power dissipation mode or power utilization mode based on the mode selected.

55. The method of claim 54, further comprising:
selecting a preference for operating the power generating leg in a power dissipation mode or a power utilization mode;
sensing that the power generating leg is in a swing phase; and
signaling the power unit to operate in one of the power dissipation mode or power utilization mode based on the mode selected.

56. A method of powering a hydraulic torque generator to generate torque between two links of a power generating leg, said power unit including a first hydraulic path between a fluid reservoir and said hydraulic torque generator having a hydraulic motor rotatably coupled to an electric generator, and a motor isolating valve connected in series, a second hydraulic path between said fluid reservoir and the hydraulic torque generator including an actuated flow restricting valve, said method comprising:
opening said motor isolating valve, powering said hydraulic motor by said electric generator and actuating the hydraulic torque generator to create a torque when said power unit is in a power utilization mode; and
closing said motor isolating valve and operating said actuated flow restricting valve to restrict the fluid flow between said hydraulic torque generator and said fluid reservoir causing said hydraulic torque generator to resist motion of said links with respect to one another when said power unit is in a power dissipation mode.

57. The method of claim 56 further comprising:
opening said power isolating valve and causing said hydraulic motor to resist a hydraulic fluid flow induced by a motion of said hydraulic torque generator and causing an electric current to pass through the terminals of said electric generator indicating that electric power is being generated by said electric generator when said power unit is in a power regeneration mode.

58. The method of claim 57, further comprising:
sensing that said power generating leg is in a stance phase and descending a stair or a slope; and
signaling said power unit to operate in said power regeneration mode.

59. The method of claim 57, further comprising:
sensing that said power generating leg is in a stance phase; and
signaling said power unit to operate in said power regeneration mode.

60. The method of claim 56, further comprising:
sensing that the power generating leg is in a stance phase and ascending a stair or a slope; and
signaling the power unit to operate in said power utilization mode.

* * * * *